United States Patent
Wiener et al.

(10) Patent No.: US 6,898,536 B2
(45) Date of Patent: May 24, 2005

(54) METHOD FOR IMPROVING THE START UP OF AN ULTRASONIC SYSTEM UNDER ZERO LOAD CONDITIONS

(75) Inventors: Eitan T. Wiener, Cincinnati, OH (US); Joseph A. Brotz, Oshkosh, WI (US); John E. Hein, Menasha, WI (US)

(73) Assignee: Etchicon Endo-Surgery, Inc., Cincinnati, OH (US)

( * ) Notice: Subject to any disclaimer, the term of this patent is extended or adjusted under 35 U.S.C. 154(b) by 175 days.

(21) Appl. No.: 10/235,952

(22) Filed: Sep. 4, 2002

(65) Prior Publication Data

US 2003/0009303 A1 Jan. 9, 2003

Related U.S. Application Data

(63) Continuation of application No. 09/866,372, filed on May 25, 2001, now Pat. No. 6,480,796.
(60) Provisional application No. 60/241,890, filed on Oct. 20, 2000.

(51) Int. Cl.[7] .............................................. G06F 13/14
(52) U.S. Cl. .............................. 702/75; 702/72; 702/74; 702/151; 702/171
(58) Field of Search ............................. 702/72, 74, 75, 702/151, 171, 39, 25, 65, 71, 106, 117, 126; 600/438; 62/51.1; 606/169

(56) References Cited

U.S. PATENT DOCUMENTS

| | | | |
|---|---|---|---|
| 2,917,691 A | 12/1959 | DePrisco et al. | 318/118 |
| 4,965,532 A | 10/1990 | Sakurai | 331/4 |
| 5,001,649 A | 3/1991 | Lo et al. | 364/484 |
| 5,026,387 A * | 6/1991 | Thomas | 606/169 |
| 5,112,300 A | 5/1992 | Ureche | 604/22 |
| 5,180,363 A | 1/1993 | Idemoto et al. | 202/32 |
| 5,400,267 A | 3/1995 | Denen et al. | 364/552 |
| 5,425,704 A | 6/1995 | Sakurai et al. | 604/22 |
| 5,449,370 A | 9/1995 | Vaitekunas | 606/169 |
| 5,630,420 A | 5/1997 | Vaitekunas | 128/662.03 |
| 5,707,369 A | 1/1998 | Vaitekunas et al. | 606/31 |
| 5,739,724 A | 4/1998 | Alexandre et al. | 331/1 |
| 5,879,364 A | 3/1999 | Bromfield et al. | 606/169 |
| 5,935,143 A * | 8/1999 | Hood | 606/169 |
| 5,968,007 A | 10/1999 | Simon et al. | 604/22 |
| 6,017,354 A | 1/2000 | Culp et al. | 606/170 |
| 6,019,775 A | 2/2000 | Sakurai | 606/169 |

(Continued)

FOREIGN PATENT DOCUMENTS

JP 00/175926 6/2000

OTHER PUBLICATIONS

EPO Search Report dated Feb. 16, 2004 for corresponding patent application, European Patent Application No. EP 01 30 8928.

Primary Examiner—Marc S. Hoff
Assistant Examiner—Felix Suarez
(74) Attorney, Agent, or Firm—Darby & Darby

(57) ABSTRACT

The start up performance of an ultrasonic system under zero load conditions is improved by setting a phase set point in a frequency control loop such that, at start up under zero load conditions, the phase set point intersects a point on a phase-frequency response curve which has a low positive slope. This intersection point on the phase-frequency response curve changes as the load is increased and the system Q is decreased. The controller "seeks" a target 0° impedance phase angle. The frequency of the ultrasonic generator is set to an off-resonance frequency which is lower than the resonance of any known hand piece/blade combination. In order for the drive voltage to not exceed the physical limit of the system, the drive current is set to a low level. The drive frequency is then smoothly increased in steps until the target 0° impedance phase delta is located.

20 Claims, 7 Drawing Sheets

U.S. PATENT DOCUMENTS

| | | |
|---|---|---|
| 6,024,750 A | 2/2000 | Mastri et al. ................ 606/169 |
| 6,063,050 A | 5/2000 | Manna et al. ................. 604/22 |
| 6,066,135 A | 5/2000 | Honda .......................... 606/39 |
| 6,066,151 A | 5/2000 | Miyawaki et al. .......... 606/169 |
| 6,090,123 A | 7/2000 | Culp et al. ................... 606/180 |
| 6,352,532 B1 * | 3/2002 | Kramer et al. ................ 606/41 |
| 6,436,115 B1 * | 8/2002 | Beaupre ...................... 606/169 |
| 6,458,142 B1 * | 10/2002 | Faller et al. ................. 606/169 |

* cited by examiner

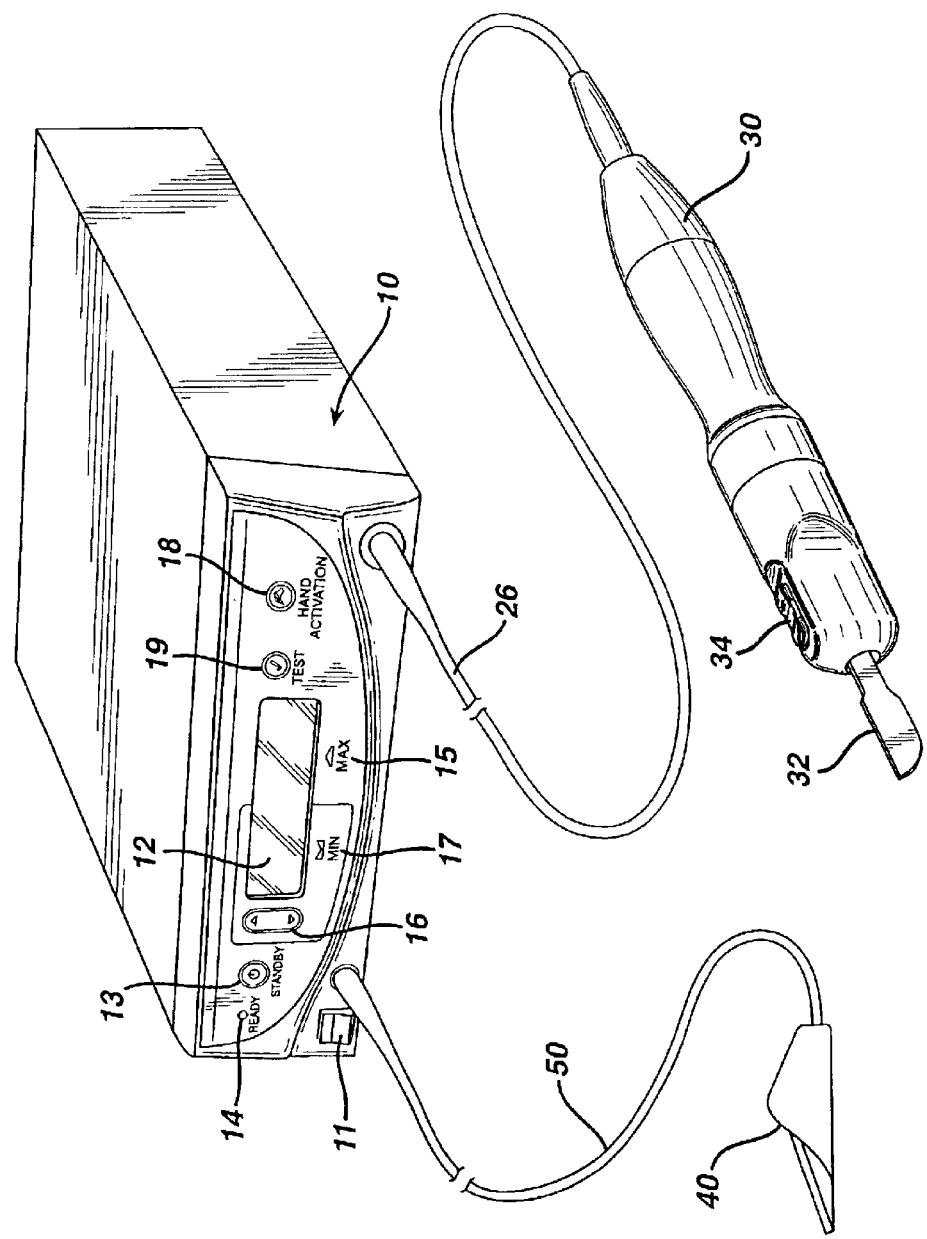

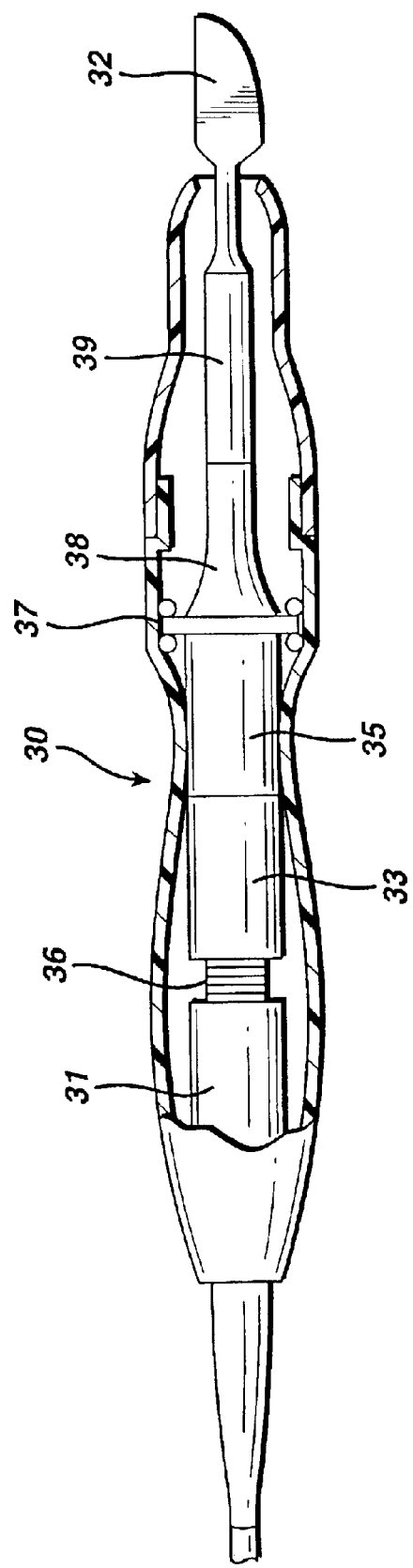

METHOD FOR IMPROVING THE START UP OF AN ULTRASONIC SYSTEM UNDER ZERO LOAD CONDITIONS

This is a continuation, of application Ser. No. 09/866,372, filed May 25, 2001 now U.S. Pat. No. 6,480,796. Each of these prior applications is hereby incorporated herein by reference, in its entirety.

RELATED APPLICATIONS

The present invention relates to, and claims priority of, U.S. Provisional Patent Application Ser. No. 60/241,890 filed on Oct. 20, 2000, and Application Ser. No. 09/866,372, filed May 25, 2001, having the same title as the present invention, which are incorporated herein by reference.

BACKGROUND OF THE INVENTION

1. Field of the Invention

The present invention generally relates to ultrasonic surgical systems and, more particularly, to a method for improving the start up of an ultrasonic system under zero load conditions.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat, as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop (that includes a voltage controlled oscillator, a frequency divider, a power switch, a matching network and a phase detector), stabilizes the frequency applied to the hand piece. A microprocessor controls the amount of power by sampling the frequency, current and voltage applied to the hand piece, because these parameters change with load on the blade.

The power versus load curve in a generator in a typical ultrasonic surgical system, such as that described in the Thomas patent, has two segments. The first segment has a positive slope of increasing power as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, continues to monitor the transducer current to voltage phase angle, and maintains the transducer resonating by driving it at the resonance frequency. A key function of such systems is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot: (i) hop over other resonance modes or make any heuristic decisions, such as what resonance(s) to skip or lock onto, and (ii) ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

The response of the blade is then determined by measuring the electrical signal supplied to the transducer when the system is in one of these modes. The ultrasonic system described in U.S. application Ser. No. 09/693,621, filed on Oct. 20, 2000, which is incorporated herein by reference, possesses the ability to sweep the output drive frequency, monitor the frequency response of the ultrasonic transducer and blade, extract parameters from this response, and use these parameters for system diagnostics. This frequency sweep and response measurement mode is achieved via a digital code such that the output drive frequency can be stepped with high resolution, accuracy, and repeatability not existent in prior art ultrasonic systems.

In an ultrasonic system, it is necessary to implement a transducer drive signal phase control method for seeking and maintaining a desired phase angle between the transducer voltage and the transducer current. In such a system, the search for the resonance frequency occurs at a predetermined frequency and phase angle which is associated with a particular transducer, and the system is accordingly set to search for a fixed point on a phase-frequency response curve, i.e., a fixed phase set point. This method is adequate for use in a system connected to a hand piece/blade which possesses a known phase-frequency response.

The phase frequency response of an unloaded hand piece/blade has a large positive slope, which makes it difficult for the phase lock loop in the generator to lock onto the resonance frequency during start up at zero load conditions. The transducer drive phase is dependent upon the frequency of the drive signal from the ultrasonic generator. However, the desired phase will not always reside at the same resonance frequency; it is dependent on the electromechanical characteristics of the transducer. These characteristics can vary from transducer to transducer, as well as with temperature changes. Accordingly, when a different hand piece/blade having a different phase-frequency response is used with the ultrasonic system, that hand piece/blade may possess a different impedance. As a result, the acquisition of lock can become even more difficult due to the system searching for the resonance at a phase set point which is associated with a another hand piece/blade.

SUMMARY OF THE INVENTION

The present invention is a method for improving the start up performance of an ultrasonic surgical system under zero load conditions. The phase set point in a frequency control loop is set such that, at start up under zero load conditions, the phase set point intersects a point on the phase-frequency response curve which has a low positive slope. This intersection point on the phase-frequency response curve changes as the load is increased and the system Q (i.e., the minimum impedance at resonance) is decreased.

In accordance with the invention, the controller "seeks" a target 0° impedance phase delta. The frequency of the ultrasonic generator is set to an off-resonance frequency which is lower than the resonance of any known hand piece/blade combination. In order for the drive voltage to not exceed the physical limit of the system, the drive current is set to a low level. The drive frequency is then smoothly increased in steps until the target 0° impedance phase delta is located.

The drive frequency step value which is used to ramp up the drive frequency is dependent upon the impedance magnitude and impedance phase of the transducer. A two dimensional lookup table, of which the impedance phase and impedance magnitude comprise two indices, contains the frequency step values for use in ramping the drive frequency. The higher the impedance magnitude and phase, the higher the interval of the drive frequency step. Once the target phase delta is obtained, it is maintained at a constant value. To accomplish this, the impedance phase and impedance magnitude are measured and used to determine a frequency correction value which is used to set the phase set point on the phase frequency response curve.

The method improves the start up of ultrasonic surgical systems having low impedance blades during no load conditions by causing the phase set point to intersect a point on a phase-frequency response curve which has a low positive slope. In addition, the method increases the flexibility of an ultrasonic system by permitting the use of hand piece/blade combinations which possess varying impedances.

BRIEF DESCRIPTION OF THE DRAWINGS

The foregoing and other advantages and features of the invention will become more apparent from the detailed description of the preferred embodiments of the invention given below with reference to the accompanying drawings in which:

FIG. 1 is an illustration of a console for an ultrasonic surgical cutting and hemostasis system, as well as a hand piece and foot switch in which the method of the present invention is implemented;

FIG. 2 is a schematic view of a cross section through the ultrasonic scalpel hand piece of the system of FIG. 1;

DETAILED DESCRIPTION OF THE PREFERRED EMBODIMENTS

Figure 3A:
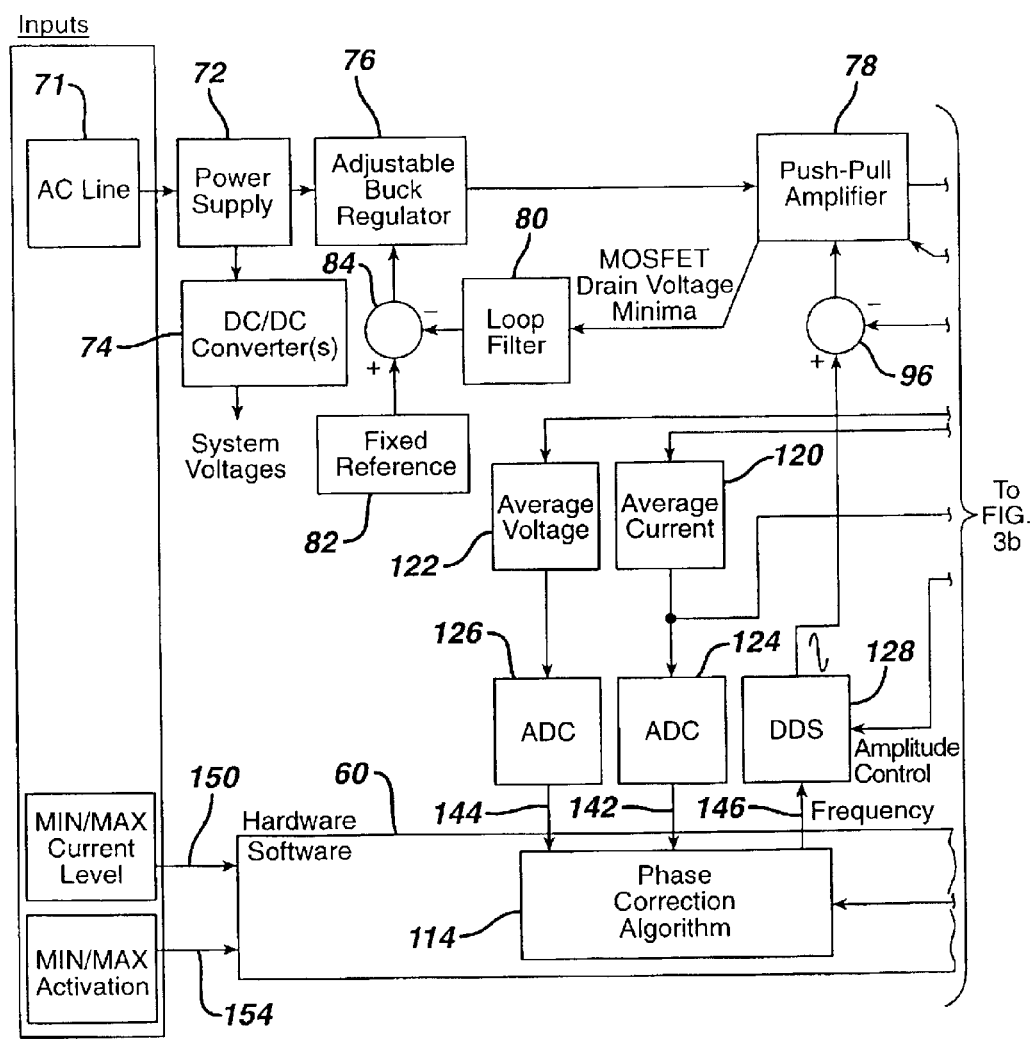
FIGS. 3(a) and 3(b) are block diagrams illustrating an ultrasonic generator in which a preferred embodiment of the invention is implemented.

FIG. 1 is an illustration of a system for implementing the method in accordance with the invention. By means of a first set of wires in cable 26, electrical energy, i.e., drive current, is sent from the console 10 to a hand piece 30 where it imparts ultrasonic longitudinal movement to a surgical device, such as a sharp scalpel blade 32. This blade can be used for simultaneous dissection and cauterization of tissue. The supply of ultrasonic current to the hand piece 30 may be under the control of a switch 34 located on the hand piece, which is connected to the generator in console 10 via wires in cable 26. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such, as percentage of maximum cutting power or numerical power levels associated with cutting power. The liquid crystal display device 12 can also be utilized to display other parameters of the system. Power switch 11 is used to turn on the unit. While it is warming up, the "standby" light 13 is illuminated. When it is ready for operation, the "ready" indicator 14 is illuminated and the standby light goes out. If the unit is to supply maximum power, the MAX button 15 is depressed. If a lesser power is desired, the MIN button 17 is activated. The level of power when MIN is active is set by button 16.

If a diagnostic test is to be performed, it is initiated by the "test" button 19. For safety reasons, e.g., to make sure a test is not started while the blade is touching the surgeon or other personnel, the button 19 must be pressed in combination with hand piece switch 34 or foot switch 40. Also, if the hand switch 34 is to be operative instead of foot switch 34, "hand activation" button 18 on the front panel must be operated.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which in turn is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node, when the transducer is driven with a current of about 380 mA RMS at the transducers' resonant frequency. However, the current providing the maximum motion will vary with each hand piece and is a valve stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into a blade movement of about 40 to 100 microns.

Figure 3B:
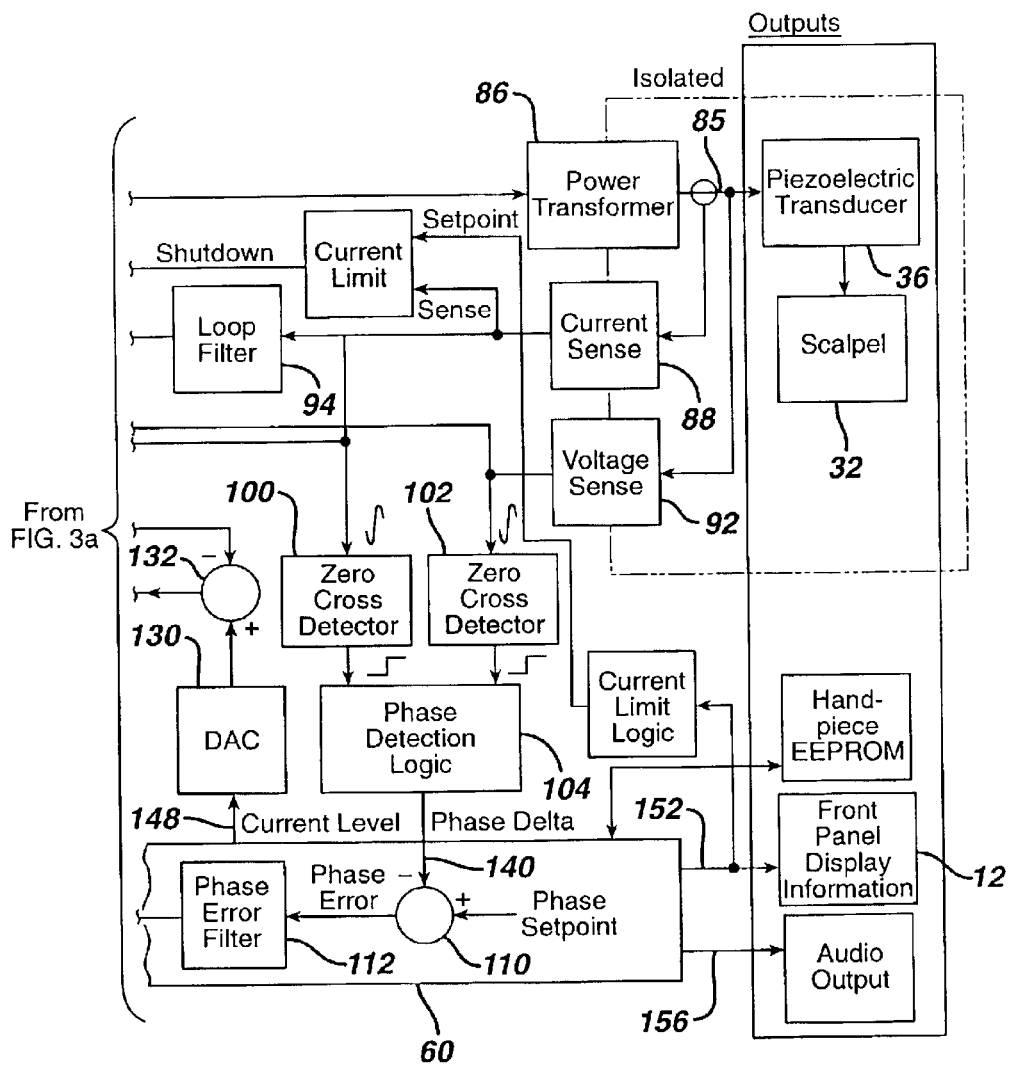

The system which creates the ultrasonic electrical signal for driving the transducer in the hand piece is illustrated in FIGS. 3(a) and 3(b). This drive system is flexible and can create a drive signal at a desired frequency and power level setting. A DSP 60 or microprocessor in the system is used for monitoring the appropriate power parameters and vibratory frequency as well as causing the appropriate power level to be provided in either the cutting or coagulation operating modes. The DSP 60 or microprocessor also stores computer programs which are used to perform diagnostic tests on components of the system, such as the transducer/blade.

For example, under the control of a program stored in the DSP or microprocessor 60, such as a phase correction algorithm, the frequency during startup can be set to a particular value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3(b)) to the console front panel display 12. Further, the DSP or microprocessor 60 generates a digital current level signal 148 that is converted to an analog signal by digital-to-analog converter (DAC) 130. The resulting reference analog signal is applied as a current set point to summing node 132. A signal representing the average output current from circuit 120 is applied to the negative input of node 132. The output of node 132 is a current error signal or amplitude control signal which is applied to direct digital synthesis (DDS) circuit 128 to adjust the amplitude of its output, as opposed to the frequency of its output, which is controlled by the signal on line 146 from the DSP or microprocessor 60. The arrangement of current level signal 148, DAC 130, summing node 130, and signal supplied by average output voltage 122 allows the DSP or microprocessor 60 to adjust the output current such that it can generate a desired power versus load curve when not in constant current mode.

To actually cause the surgical blade to vibrate, the user activates the foot switch 40 or the hand piece switch 34. This activation puts a signal on line 154 in FIG. 3(a). This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

Figure 4A:
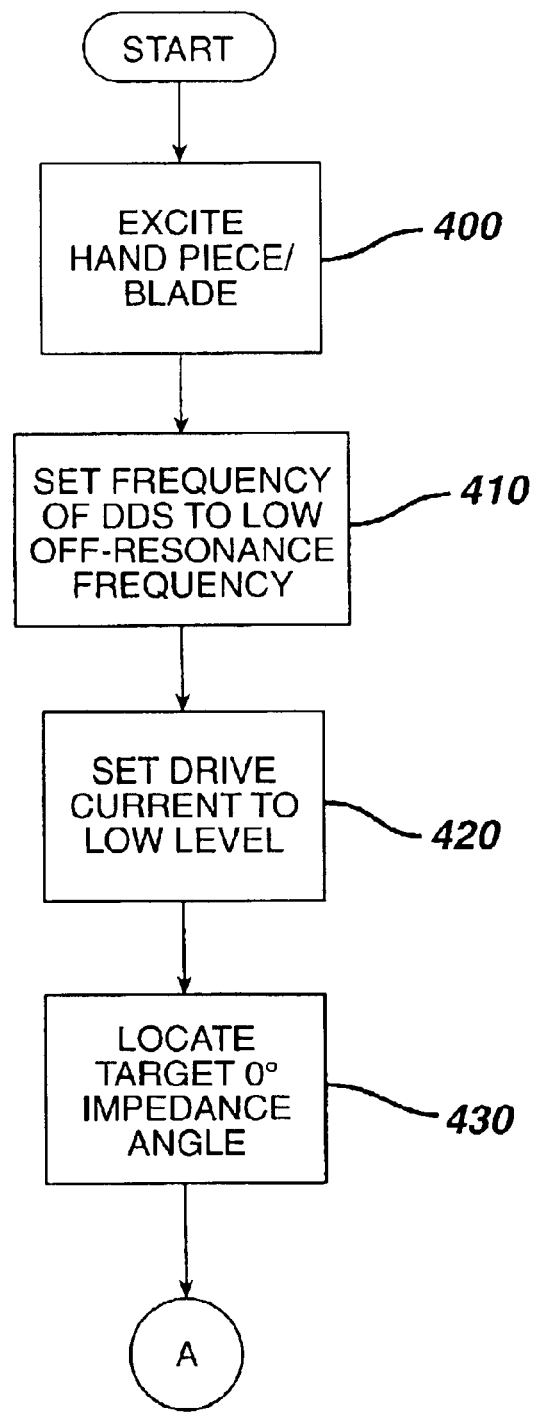
FIGS. 4(a) and 4(b) are flow charts illustrating the preferred embodiment of the method of the invention.
Figure 4B:
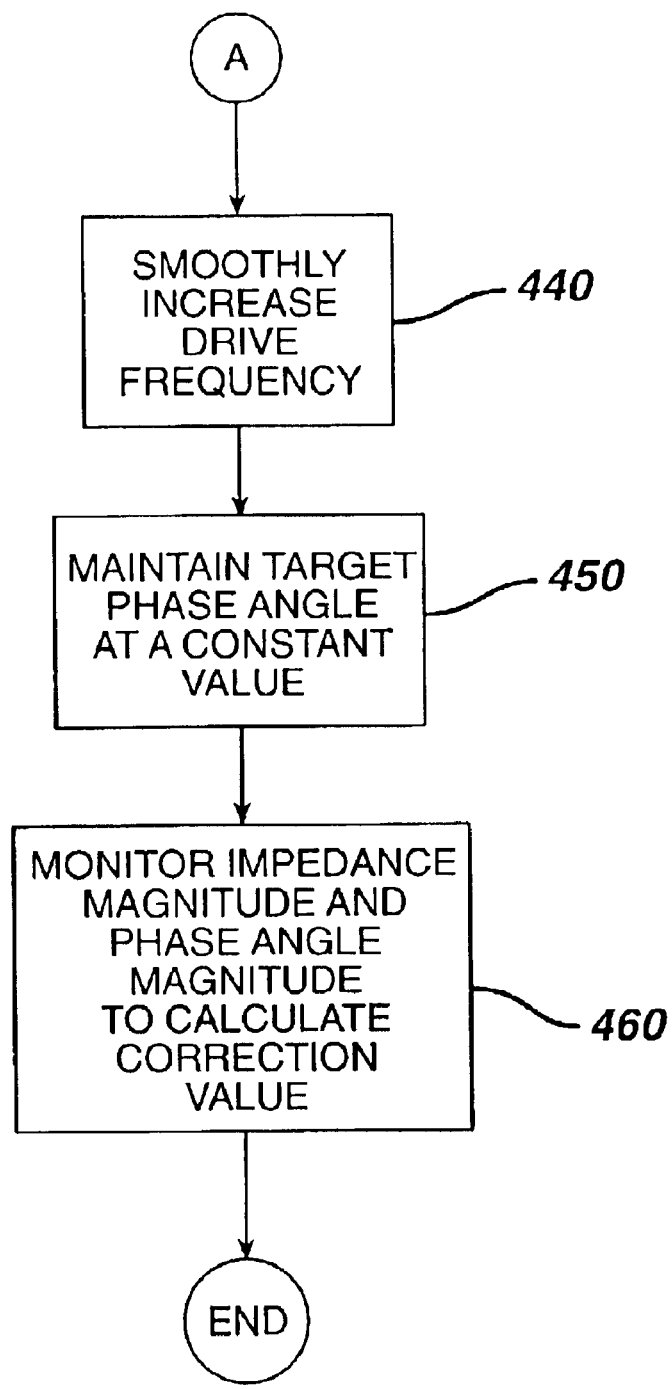

FIGS. 4(a) and 4(b) are flow charts illustrating a preferred embodiment of the method of the invention. Under control of the program stored in the DSP or microprocessor 60 shown in FIG. 3(a) and 3(b), the method of the invention is implemented by using the ultrasonic generator to excite the hand piece/blade, as indicated in step 400. The frequency of the direct digital synthesis (DDS) circuit is set to an off-resonance frequency which is lower than the resonance of any known hand piece/blade combination, as indicated in step 410. When off-resonance, the impedance magnitude of the system is very high. Accordingly, in order for the drive voltage to not exceed the physical limit of the system, the drive current is set to a low level, as indicated in step 420. In the preferred embodiment, the drive current is set to 100 mA.

Next, the phase lock loop searches for a target 0° impedance phase angle (φ), as indicated in step 430. The drive frequency is smoothly increased in steps until the target 0° impedance phase angle is located, as indicated in step 440. As the resonance of the hand piece/blade is approached, a corresponding reduction in the impedance magnitude occurs. Here, the current set point can be raised to a point where the voltage magnitude falls just below the physical limit of the system. The frequency must be smoothly ramped to avoid oscillation of the impedance magnitude and impedance phase angle of the hand piece/blade. Oscillation occurs when the search to locate the target 0° impedance phase angle results in a rate of change of displacement (d/dt) which exceeds the maximum dφ/dt which occurs in the natural mechanical resonance of the hand piece/blade.

The drive frequency step value which is used is dependent upon the impedance magnitude and impedance phase of the transducer. The difference in frequency of the anti-resonance (frequency with maximum impedance) and the resonance (frequency with minimum impedance) is the "phase margin," which is measured in hertz. A two dimensional lookup table, of which the impedance phase and impedance magnitude comprise two indices, contains the frequency step values for use in ramping the level of the drive frequency. The higher the impedance magnitude and impedance phase, the higher the interval of the drive frequency step. An exemplary frequency step value at a particular phase and magnitude stored in the look-up table is 20 Hz. In the preferred embodiment, the frequency step is applied at a rate 2KHz or greater.

In order to obtain the impedance and impedance phase measurements, the DSP 60 and the other circuit elements of FIGS. 3(*a*) and 3(*b*) are used. In particular, push-pull amplifier 78 delivers the ultrasonic signal to a power transformer 86, which in turn delivers the signal over a line 85 in cable 26 to the piezoelectric transducers 36 in the hand piece. The current in line 85 and the voltage on that line are detected by current sense circuit 88 and voltage sense circuit 92. The current and voltage sense signals are sent to average voltage circuit 122 and average current circuit 120, respectively, which take the average values of these signals. The average voltage is converted by analog-to-digital converter (ADC) 126 into a digital code that is input to DSP 60. Likewise, the current average signal is converted by analog-to-digital converter (ADC) 124 into a digital code that is input to DSP 60. In the DSP the ratio of voltage to current is calculated on an ongoing basis to give the present impedance values as the frequency is changed. A significant change in impedance occurs as resonance is approached.

The signals from current sense 88 and voltage sense 92 are also applied to respective zero crossing detectors 100, 102. These produce a pulse whenever the respective signals cross zero. The pulse from detector 100 is applied to phase detection logic 104, which can include a counter that is started by that signal. The pulse from detector 102 is likewise applied to logic circuit 104 and can be used to stop the counter. As a result, the count which is reached by the counter is a digital code on line 104, which represents the difference in phase between the current and voltage. The size of this phase difference is also an indication of resonance. These signals can be used as part of a phase lock loop that cause the generator frequency to lock onto resonance, e.g., by comparing the phase angle to a phase set point in the DSP in order to generate a frequency signal represented by a binary number to a direct digital synthesis (DDS) circuit 128 that drives the push-pull amplifier 78. Alternatively, a drive signal may be provided to the push-pull amplifier 78 using a Voltage Controlled Oscillator (VCO) as is known by those skilled in the art.

Figure 5:
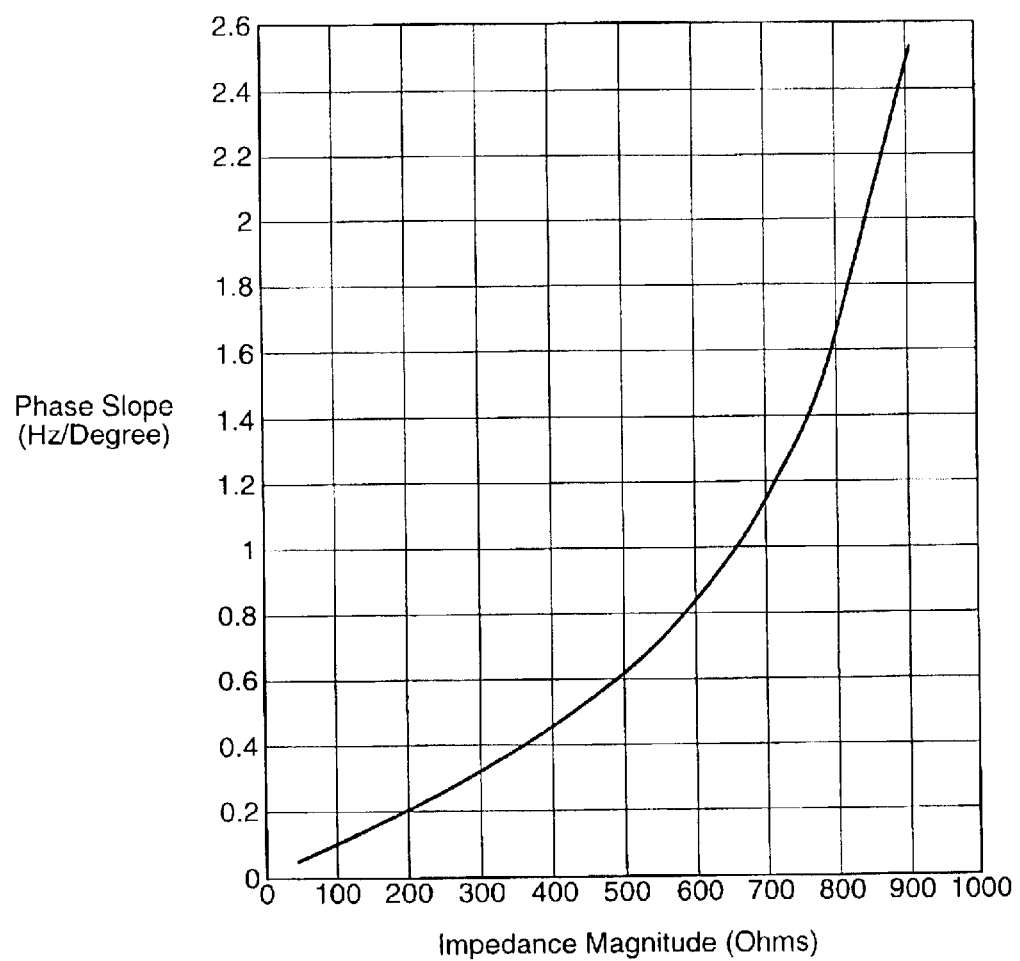
FIG. 5 is a plot of a phase-slope vs. impedance relationship for a hand piece/blade at 0° impedance phase.

Once the target phase angle is obtained, it is maintained at a constant value, as indicated in step 450. The resonance frequency at which the target 0° impedance phase angle occurs can drift due to changes in temperature of the hand piece/blade, or it can move rapidly due to changes in the mechanical load at the hand piece/blade. To maintain the 0° impedance under these conditions, the impedance phase angle and impedance magnitude are monitored and used to calculate a frequency correction value in accordance with a phase-slope vs. impedance relationship of a hand piece at 0° impedance phase angle shown in FIG. 5, as indicated in step 460. This calculation is performed in accordance with the relationship:

$$f_\Delta = \phi * \text{phase\_slope} (|z|) * k,$$

where $f_\Delta$ is the calculated frequency correction value, φ is a phase reading, z is impedance in ohms, and k is a scaling factor. Note, the phase slope curve shown in FIG. 5 does not significantly change within a range of approximately ±40° centered about the 0° phase angle. Accordingly, the curve is applicable even when the method of the invention is performed at frequencies which are slightly off-resonance. The scaling factor k is a fractional number less than 1 which is applied to prevent overshoot and is used to compensate for delays introduced while filtering the impedance phase angle and impedance magnitude measurements. The impedance magnitude and phase reading are filtered with a moving window average routine. This correction functional is applied at a 1 KHz rate.

Using the method of the invention, the start up of an ultrasonic surgical system during no load conditions is improved, due to the adaptive resetting of the phase set point to a position on the phase-frequency response curve which has a low positive slope.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for improving start up performance of an ultrasonic surgical system under zero load conditions, comprising the steps of:

applying a drive signal from an ultrasonic generator to a hand piece/blade;

adjusting a circuit located in the generator;

performing a first search to locate a target angle;

increasing a drive frequency of the drive signal;

maintaining the target angle at a constant value;

monitoring properties of the drive signal at the increased drive frequency to calculate a differential value; and adjusting the circuit using the calculated differential value.

2. The method of claim 1, wherein the step of adjusting the circuit comprises adjusting a frequency of the circuit.

3. The method of claim 1, wherein said circuit is adjusted to an off-resonance frequency of the hand piece/blade.

4. The method of claim 2, wherein the frequency of the circuit is an off-resonance frequency of the hand piece/blade.

5. The method of claim 2, wherein the circuit is a direct digital synthesis circuit located in the generator.

6. The method of claim 1, further comprising the step of:
adjusting the drive signal of the ultrasonic generator to a low level.

7. The method of claim 1, wherein said performing step comprises searching for the target angle.

8. The method of claim 7, wherein the target angle is a 0° impedance phase angle.

9. The method of claim 1, wherein said applying step comprises the steps of:
exciting the hand piece/blade with a drive current using the ultrasonic generator at an initial drive frequency; and
setting the drive current to a low level.

10. The method of claim 1, wherein said maintaining step comprises maintaining the target 0° impedance phase angle at the constant value.

11. The method of claim 1, wherein said monitoring step comprises monitoring properties of the drive signal at the increased drive level to calculate the frequency differential.

12. The method of claim 11, wherein the drive signal properties are impedance and phase angle magnitude values.

13. The method of claim 1, wherein the drive signal properties are impedance and phase angle magnitude values.

14. The method of claim 1, wherein said adjusting step comprises correcting the circuit using the calculated differential value.

15. The method of claim 9, wherein the step of setting the drive current to a low level comprises the step of:
applying a drive current having a level of 100 ma.

16. The method of claim 7, wherein the step of searching for the target angle, comprises the step of:
increasing a frequency of the drive signal smoothly in predetermined steps until the target angle is located;
wherein the drive frequency is smoothly increased to avoid impedance magnitude and impedance phase angle oscillations of the hand piece/blade.

17. The method of claim 3, wherein the predetermined step is 20Hz and is applied at a rate of at least 2 kHz.

18. The method of claim 1, wherein said calculation of the calculated differential value is performed in accordance with a phase-slope vs. impedance relationship of a hand piece at 0° impedance phase angle.

19. The method of claim 18, wherein the phase-slope vs. impedance relationship comprises the relationship:

$$f\Delta = \phi * \text{phase\_slope}(|z|) * k,$$

wherein $f\Delta$ is the calculated frequency correction value, $\phi$ is a phase reading, z is impedance in ohms, and k is a scaling factor.

20. The method of claim 19, wherein the scaling factor is a fractional number having a magnitude of less than 1.

* * * * *

UNITED STATES PATENT AND TRADEMARK OFFICE
CERTIFICATE OF CORRECTION

PATENT NO. : 6,898,536 B2
DATED : May 24, 2005
INVENTOR(S) : Eitan T. Wiener et al.

It is certified that error appears in the above-identified patent and that said Letters Patent is hereby corrected as shown below:

Title page,
Item [73], Assignee, please delete "Etchicon Endo-Surgery, Inc., Cincinnati, OH (US)" and substitute -- Ethicon Endo-Surgery, Inc., Cincinnati, OH (US) --.

Signed and Sealed this

Ninth Day of August, 2005

JON W. DUDAS
*Director of the United States Patent and Trademark Office*